(12) United States Patent
Werner et al.

(10) Patent No.: US 7,498,551 B2
(45) Date of Patent: Mar. 3, 2009

(54) APPARATUS AND METHOD FOR TRACKING A MOLECULE OR PARTICLE IN THREE DIMENSIONS

(75) Inventors: James H. Werner, Los Alamos, NM (US); Peter M. Goodwin, Los Alamos, NM (US); Guillaume Lessard, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 238 days.

(21) Appl. No.: 11/544,988

(22) Filed: Oct. 6, 2006

(65) Prior Publication Data

US 2008/0085550 A1    Apr. 10, 2008

(51) Int. Cl.
*G01N 21/64* (2006.01)

(52) U.S. Cl. .................... 250/203.2; 250/201.3

(58) Field of Classification Search ............. 250/201.3, 250/203.2, 203.3
See application file for complete search history.

(56) References Cited

OTHER PUBLICATIONS

Saxton et al., "Single-Particle Tracking: Applications to Membrane Dynamics," Annual Review of Biophysics and Biomolecular Structure, Jun. 1997, vol. 26, pp. 373-399.
Kao et al., "Tracking of Single Fluorescent Particles in 3 Dimensions: Use of Cylindrical Optics to Encode Particle Position," Biophysical Journal, Sep. 1994, vol. 67, No. 3, pp. 1291-1300.
Dickson et al., "Three-Dimensional Imaging of Single Molecules Solvated in Pores of Poly(acrylamide) Gels," Science, Nov. 1996, vol. 274, No. 5289, pp. 966-969.
Braun et al., "Fluorescence Interference-Contrast Microscopy of Cell Adhesion on Oxidized Silicon," Applied Physics A (Material Science Processing), Oct. 1997, vol. 65, Vol. 4/5, pp. 341-348.
Ajo-Franklin et al., "Variable Incidence Angle Fluorescence Interference Contrast Microscopy for Z-Imaging Single Objects," Biophysical Journal, Oct. 2005, vol. 89, No. 4, pp. 2759-2769.
Prabhat et al., "Simultaneous Imaging of Different Focal Planes in Fluorescence Microscopy for the Study of Cellular Dynamics in Three Dimensions," IEEE Transactions on Nanobioscience, Dec. 2004, vol. 4, No. 4, pp. 237-242.
Enderlein, "Tracking of Fluorescent Molecules Diffusing Within Membranes," Applied Physics B-Lasers and Optics, Nov. 2000, vol. 71, No. 5, pp. 737-777.
Enderlein, "Positional and Temporal Accuracy of Single Molecule Tracking," Single Molecules, Sep. 2000, vol. 1, No. 3, pp. 225-230.
Levi et al., "3-d Particle Tracking in a Two-Photon Microscope: Application to the Study of Molecular Dynamics in Cells," Biophysical Journal, Apr. 2005, vol. 88, No. 4, pp. 2919-2928.

(Continued)

*Primary Examiner*—F. L Evans
(74) *Attorney, Agent, or Firm*—Samuel L. Borkowsky

(57) ABSTRACT

An apparatus and method were used to track the movement of fluorescent particles in three dimensions. Control software was used with the apparatus to implement a tracking algorithm for tracking the motion of the individual particles in glycerol/water mixtures. Monte Carlo simulations suggest that the tracking algorithms in combination with the apparatus may be used for tracking the motion of single fluorescent or fluorescently labeled biomolecules in three dimensions.

20 Claims, 4 Drawing Sheets

OTHER PUBLICATIONS

Visscher et al., "Versatile Optical Traps With Feedback Control," Methods in Enzymology; Molecular Motors and the Cytoskeleton, part b, Aug. 1998, vol. 298, pp. 460-489, R. Vallee, Editor, 1998, 14 Belgrave Square, 24-28 Oval Road, London NW1 70X, England, UK: Academic Press Ltd.

Michalet et al., "Quantum Dots for Live Cells, In Vivo Imaging, and Diagnostics," Science, Jan. 2005, vol. 307, No. 5709, pp. 538-544.

Wu et al., "Three-Dimensional Fluorescent Particle Tracking at Micron-Scale Using a Single Camera," Experiments in Fluids, Feb. 2005, vol. 38, pp. 461-465.

Berglund et al., "Tracking-FCS; Fluorescence Correlation Spectroscopy of Individual Particles," Oct. 2005, vol. 13, No. 20, Optics Express pp. 8069-8082.

APPARATUS AND METHOD FOR TRACKING A MOLECULE OR PARTICLE IN THREE DIMENSIONS

STATEMENT REGARDING FEDERAL RIGHTS

This invention was made with government support under Contract No. DE-AC52-06NA-25396 awarded by the U.S. Department of Energy. The government has certain rights in the invention.

FIELD OF THE INVENTION

The present invention relates generally to fluorescence microscopy and more particularly to an apparatus and method for tracking a single fluorescent or fluorescently tagged molecule or particle in three dimensions.

BACKGROUND OF THE INVENTION

Single molecule detection by laser-induced fluorescence has emerged as a powerful tool for the characterization and measurement of biological processes. Single molecule measurements have been used to investigate enzymatic turnovers, to study the exact step size of molecular motors, and to observe the diffusion and transport of lipids and receptors on cellular membranes. Much has been learned from these single-molecule studies that had been obscured in ensemble measurements of the same processes, including for example, evidence of history dependent conformations of individual enzymes, the precise step size taken by individual motor proteins, and evidence for hindered diffusion created by domain structure within a cellular membrane [1]. In all of these examples, the motion of the molecule under investigation was limited to zero, one, or two dimensions.

While single molecule tracking in two dimensions has contributed fundamentally to an understanding of cell membrane dynamics, organization, and transport [1] it is important that single molecule imaging techniques be extended from 2 dimensions to 3 dimensions because most aspects of life, such as intracellular signaling and trafficking are three dimensional.

An approach for tracking the 3-dimensional motion of a molecule is to use a series of 2-dimensional images that have the optical signature of the molecule and vary in a measurable fashion with its distance perpendicular to the image plane [2, 3, 4, 5]. The extension of single particle tracking in three dimensions using a series of two-dimensional images has been reported. These studies relied on the fact that the optical signal can vary dramatically and measurably with the distance from the image plane of the sample. One such study involved the use of total internal reflection (TIR) excitation. In TIR excitation, an evanescent wave that is created at a TIR interface is used for fluorescence excitation. The excitation intensity falls off exponentially from the TIR interface with a decay constant on the order of about 100 nm. The intensity of an object reports its position in the direction perpendicular to the image plane, while its "XY" position is determined from its position in the image itself. TIR microscopy has been used to determine the three dimensional position of single GFP molecules suspended in a polymer matrix [3]. A problem with the TIR method is that it is limited to observing the motion of objects that are within about 100 nm of an interface that has a mismatch in the index of refraction. For many biological applications, such as tracking intra-cellular transport or diffusion, this limitation is too restrictive.

In an alternative approach to 3-dimensional tracking, two separate image planes are created in a sample space [6]. This effectively doubles the depth of focus of a microscope such that dynamics can be followed over an extended z range. This extension in z can be useful, for example, to follow dynamics above and below a cell membrane interface for trans-membrane events such as exocytosis. A disadvantage of this approach is that reading out an entire CCD chip takes a substantial amount of time. In addition, reading out the entire CCD chip introduces noise as charges are swept from pixel to pixel, and crude image processing must be used to find the molecule of interest. In the time needed to read-out the CCD chip, process the image, and potentially move to follow the z-motion of the molecule, the molecule of interest likely will have diffused entirely out of the focal plane of the microscope.

Enderlein proposed a method of tracking single molecules in two dimensions using a single photon counting avalanche photodiode as the detection source and an excitation laser beam that sweeps a small circle in the image plane of a microscope objective [7, 8]. With each sweep of the excitation laser, the fluorescence intensity would be a maximum at a certain angular value. The microscope stage would then be moved to position the single molecule in the center of the circle of excitation swept by the laser beam. Levi et al. extended Enderlein's proposed method in order to follow 3-dimensional trajectories [9]. The Levi et al. approach involves four circular sweeps of an excitation laser, with two sweeps above and the other two below the particle being tracked. The intensity profile recorded during these sweeps is used to control a piezo-stage to reposition the object closer to the center of the optical probe volume. Levi et al. demonstrated the 3-dimensional tracking of 0.5 µm diameter fluorescent microspheres in glycerol-water mixtures and followed the phagocytosis of protein-coated beads by fibroblasts. While the method seems promising, it appears to be useful for tracking only very bright particles that are decorated with perhaps thousands of fluorescein equivalents. This limitation stems from the duty cycle of the tracking algorithm. Most of the time the excitation laser isn't exciting the molecule; it is searching for it. The limited number of photons detected by a rapid sweep over a single fluorescent molecule makes this method difficult to implement for single molecule applications.

The extension of single molecule tracking 2-dimensional motion to 3-dimensional spatial trajectories will allow the study of intra-cellular spatial and temporal dynamics such as DNA damage repair pathways, cellular signaling, regulatory networks, or protein trafficking. There is presently no apparatus or method for tracking a molecule in three dimensions by the fluorescence output of the molecule.

There remains a need for an apparatus and method for tracking a molecule or particle in three dimensions by the fluorescence output of the molecule or particle.

SUMMARY OF THE INVENTION

In accordance with the purposes of the present invention, as embodied and broadly described herein, the present invention includes an apparatus for tracking the position of a chosen molecule or particle in a sample. The apparatus includes a stage for supporting the sample, a light source for emitting a light beam capable of inducing a measurable light-based response from a chosen molecule or particle in the sample, and an objective lens for focusing the light beam on the sample to create an excitation volume. The objective lens projects at least a portion of the light based response from the excitation volume to at least one image plane. The apparatus also includes a dichroic element for directing the light beam from the light source to the objective lens, at least one spatial filter at the at least one image plane for selecting a portion of the light based response and defining an optical probe volume for that portion of the light based response, means for introducing a controlled relative motion between the optical probe volume and the molecule or particle, and means for monitoring the light based response from the chosen molecule or particle. The means for monitoring the light based response uses the light based response to control an overlap between the optical probe volume with the particle or molecule being tracked. The measurable light-based response can be, for example, light emission or light scattering. An example of a light emission monitored using the apparatus is fluorescence. One or more of the spatial filters may be moveable.

The invention also includes an apparatus for tracking the position of a chosen molecule or particle in a sample. The apparatus includes a stage for supporting the sample, a light source for emitting a light beam capable of inducing a light based response from a chosen molecule or particle in a sample, and an objective lens for focusing the light beam on the chosen molecule or particle in the sample. The apparatus also includes means for introducing a controlled lateral displacement between said light source and said stage, a dichroic element for directing the light beam from said light source to said objective lens, and means for creating at least a first image plane and a second image plane. The first image plane includes spatial information from a first portion of the sample. The second image plane includes spatial information from a second portion of the sample, and the first portion and second portion define an optical probe volume. The apparatus also includes a first optical spatial filter that sends light from the first image plane to a first photon detector and a second optical spatial filter that sends light from the second image plane to a second photon detector. The apparatus also includes a first photon detector that receives light from the first image plane and a second photon detector that receives light from second image plane. The apparatus also includes means for analyzing light from the first detector and the second detector. The means for analyzing light uses an analysis of light from the first photon detector and the second photon detector to control an overlap between the optical probe volume and the particle or molecule being tracked. The stage of the apparatus may be moveable in order to adjust the position of the molecule or particle being tracked. Examples of the light-based response include light emission or light scattering. An example of light emission is fluorescence.

The invention also includes an apparatus for tracking the position of a chosen molecule or particle in a sample. The invention includes a light source for emitting a light beam capable of inducing fluorescence from a chosen molecule or particle in a sample, an objective lens for focusing the light beam on the chosen molecule or particle in the sample, a stage for supporting the sample, and a dichroic element for directing the light beam from the light source to the objective lens. The apparatus also includes means for creating a first image plane and a second image plane. The first image plane includes spatial information from a first portion of the sample, and the second image plane is nearly conjugate with the first image plane and includes spatial information from a second portion of the sample. The first portion and second portion define an optical probe volume. The apparatus also includes a first optical fiber that sends light from the first image plane to a first photon detector (the first optical fiber has a cross-section with a center), a second optical fiber that sends light from the first image plane to a second photon detector (the second optical fiber has a cross-section with a center). A line that connects the center of the first optical fiber and the center of the second optical fiber is parallel to the x-axis. The apparatus also includes a third optical fiber that sends light from the second image plane to a third detector (the third optical fiber has a cross-section with a center), and a fourth optical fiber that sends light from the second image plane to a fourth detector (the fourth optical fiber has a cross-section with a center), and a line connecting the center of third optical fiber and the center of the fourth optical fiber is parallel to the y axis. The apparatus also includes means for reading photon counts from fluorescence detected by the first detector and the second detector and the third detector and the fourth detector. The means for reading photon counts uses the photon counts to control the overlap between the optical probe volume and the particle or molecule being tracked.

The invention also includes a method for tracking the position of a chosen particle or molecule in a sample. The method includes exposing a sample to light to induce fluorescence from a chosen particle or molecule in the sample, the sample comprising a plurality of z-slices that define an optical probe volume; analyzing the fluorescence with a first image plane that includes spatial information from a first z-slice from the plurality of z-slices, and with a second image plane that is nearly conjugate with the first image plane, the second image plane including spatial information from a second z-slice from the plurality of z-slices; and using the spatial information from the first image plane and the second image plane to control the overlap of the optical probe volume and the particle or molecule being tracked.

The invention also includes a method for tracking the position of a chosen particle or molecule in a sample. The method includes exposing a sample to light for a chosen period of time to induce light emission from a particle or molecule in the sample; detecting the light emission using a plurality of detectors; and using the intensity of the light emission to evaluate the distance between the center of an optical probe volume and the molecule or particle being tracked.

The invention also includes a method for tracking a molecule in three dimensions. The method includes exposing a sample to light for a chosen period of time to induce light emission from a chosen particle or molecule in the sample; detecting the light emission using a plurality of detectors, each of said plurality recording the light emission at a different location near the sample; determining which of the plurality of detectors detected the highest light emission during the chosen period of time; and adjusting the position of the sample away from the detector that detected the highest light emission and toward the other detectors of the plurality of detectors.

Light sources used with the invention include, but are not limited to, a diode, an arc lamp, a tungsten filament, and the like.

BRIEF DESCRIPTION OF THE DRAWINGS

The accompanying drawings, which are incorporated in and form a part of the specification, illustrate the embodiment(s) of the present invention and, together with the description, serve to explain the principles of the invention. In the drawings.

DETAILED DESCRIPTION

Figure 1:
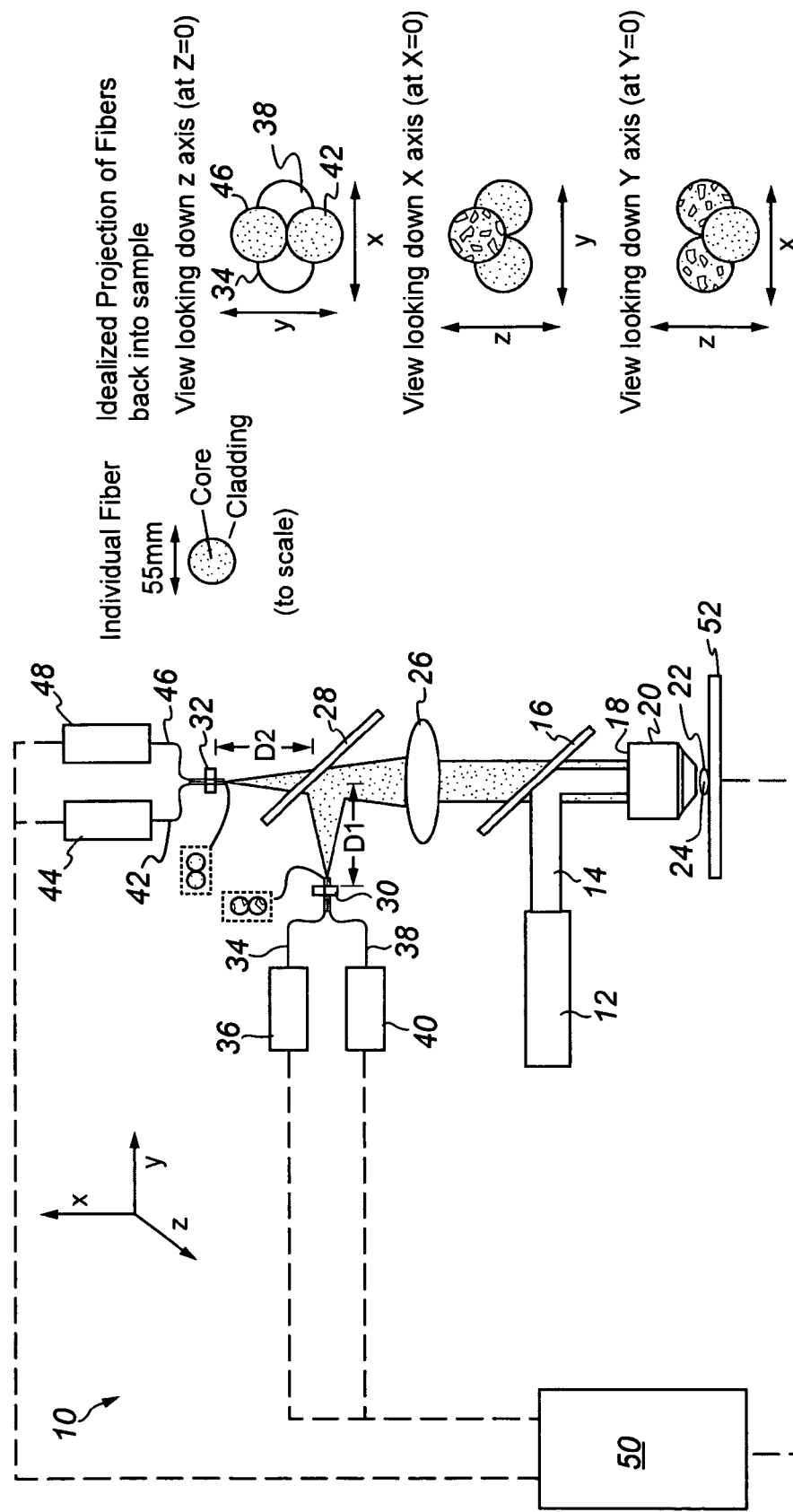
FIG. 1 shows a schematic diagram of an embodiment apparatus of the present invention for tracking single molecules by their fluorescence.

Briefly, the invention is concerned with tracking the spatial position of a molecule or particle in three dimensions by the fluorescence of the molecule or particle. The invention may be used to study the same molecule or particle for an extended period of time. The observation window is limited by photobleaching of a fluorescent reporter. Using the invention, molecules or particles may be studied on timescales that are orders of magnitude longer than what is generally measured in solution. Rare events or conformations may be observed. An added benefit of increased observation time is an increase in the number of photons detected from a single molecule. The limited number of photons measured from a single molecule generally limits the measurement precision. Measurements made on a tracked single molecule using the invention are more precise because they are based on the maximum number of detected photons. The stage may be moveable in order to adjust the position of the molecule or particle being tracked. The apparatus may also include means for splitting the light based response from the excitation volume to a first image plane and to a second image plane. Examples of means for splitting the light based response include a beamsplitter or a dichroic filter.

Time-correlated single photon counting is used for measuring the fluorescence lifetime of single molecules being tracked. The fluorescence lifetime of the molecule being tracked may reflect changes in the molecular environment of a fluorophore. Depending on the fluorescent reporter, the excited state lifetime can reflect changes in the local pH, membrane potential, changes in the energy transfer efficiency, and the like. The fluorescence lifetime is sensitive to changes in the local environment surrounding the fluorophore.

Our approach to the 3-dimensional tracking of a molecule or particle involves the use of small arrays of single photon-counting avalanche photodiodes (SPADs) to sense and measure displacements in a confocal optical detection volume. In a preferred embodiment, four of these photodiodes are used. These four photodiodes are arranged in two separate image planes (each plane has 2 detectors), with these 2 image planes being slightly offset in the "z" direction are used to sense displacements of a molecule or particle from the center of a detection volume. The employment of this type of optical detection provides the necessary speed, 3-dimensional sectioning capability, and detection sensitivity for tracking single molecules as they move in three dimensions.

An embodiment of the invention employs two small fiber arrays. Each fiber leads to an independent SPAD. The invention also employs a computer controlled, fast, closed loop, XYZ piezo stage. A sample that includes the molecule or particle being tracked is on the piezo stage. The computer runs a digital feedback loop in order to keep a molecule or particle being tracked in the center of the field of view.

Having briefly described certain aspects of the invention, a more detailed description of the invention now follows.

The invention is concerned with an apparatus, tracking algorithms, and software for tracking the movement of a single molecule or particle in three dimensions. An embodiment apparatus useful for this type of tracking is based on a confocal microscopic platform. In this embodiment, an excitation laser is reflected by a dichroic into the back of a high numerical aperture microscope objective, forming a near diffraction limited spot in the sample space. The laser light interacts with a molecule or particle and induces fluorescence emission from the molecule or particle. The same objective used for fluorescence excitation also collects the emitted light. The fluorescence signal is split, and different portions of the fluorescence are sent to two different image planes. Each image plane has two spatial filters (in a preferred embodiment, these are fiber optics) with each spatial filter leading to a single element photon detector, such as a SPAD. Each of the four detectors counts single photons. A computer system (or a field programmable gate array (FPGA), for example) uses the counts on the four detectors to (i) estimate the position of a molecule and (ii) move the piezo stage of the microscope to re-position the molecule or particle that is being tracked back to the center of an excitation volume.

Preferably, single element detectors are used with the invention. Preferred detectors are single photon counting avalanche photodiodes. Single element detectors are superior to camera-based tracking approaches because single element detectors (1) have zero read noise, (2) enable time-resolved (fluorescence lifetime) measurements of the molecule being tracked, (3) are "faster" than cameras, and (4) allow real-time feedback.

In a typical embodiment, the optical fibers in the image planes have a core diameter of 50 microns and a cladding diameter of 55 microns. The output of each fiber is focused onto a single photon counting avalanche photodiode (SPAD), which is a high quantum yield (about 50% in the visible) single photon counting detector that outputs a TTL (transistor-transistor logic) level voltage pulse for every detected photon. Each fiber in the image plane of the objective acts as a confocal aperture that limits the field of view of its associated detector. The distance of each of the two fiber bundles to the back of the objective is slightly different. This offset in optical path length results in each fiber pair viewing a different "z" location in the sample space. The two sets of fibers are rotated 90 degrees with respect to each other. Image plane 1 (black fibers) has a linear bundle oriented vertically, whereas image plane 2 (grey fibers) has a linear bundle oriented horizontally. As the lateral dimensions of these fibers are on the order of 50 µm, the projection of these confocal apertures into the sample plane is on the order of about one µm, as a 60×1.2 numerical aperture (NA) water immersion objective is employed. All four detection regions are simultaneously excited with substantially the same intensity, so slightly larger excitation probe volumes (by a factor of 2-3) are used with this embodiment than what is typically used in standard confocal microscopy.

In an alternative embodiment, a pinhole, rather than an optical fiber, may be used in the image plane of the objective-tube lens system as the spatial filter. A confocal excitation and detection geometry enables optical sectioning in three dimensions, as the pinhole rejects out of focus light that originates from different z planes in the sample.

Light emitted by a single molecule in the exact center of the optical probe volume is split equally amongst four different fibers/detectors. A movement of the molecule out of the center of the probe-volume leads to unequal count distributions on the four detectors. A computer system monitors the counts on the four detectors. The computer system controls a fast, closed-loop piezo positioning stage (PI 733-3DD) having sub-nanometer accuracy. The purpose of this digital feedback loop is to keep the counts as equal and as high as possible on all detectors. Feedback control using small arrays of single element detectors has been used in the control of laser tweezers [10]. For tweezer applications, quadrant photodiode arrays are used to monitor lateral displacements. Quadrant photodiodes are not believed to be sensitive enough for the low-light application of single molecule tracking of the present invention. Instead, small arrays of fiber bundles leading to independently addressable SPADs are preferred with the present invention.

To keep a molecule or particle in the center of the optical probe volume, the stage is moved in the opposite direction and at the same velocity that the molecule under investigation is traveling. The general direction the molecule is traveling can be determined from the count distribution amongst the four detectors. A simple approximation is that the detector that has the most counts of the four reflects the direction in which the molecule is moving out of the optical probe volume. A computer measures the photon counts on all four detectors and moves the stage to position the molecule away from the detector with the most counts (the "hot" detector) and closer towards the center of the optical probe volume. During the next time step, the molecule would be moved away from the new "hot" detector towards the other remaining three. This tracking algorithm is essentially a game of "hot-potato" amongst the four detectors, where each detector tries to "push" the molecule away from it and towards the other three by moving the piezo stage.

Optimizing the tracking parameters for a single molecule or particle depends on many variables. The tracking parameters depend, for example, on the size and shape of the molecule or particle being tracked, the integration time, the size/spacing of the fibers in the image plane, the overall system magnification, among other things. The integration time, for example, should be long enough to obtain a precise measurement of the particle's position, but short enough so that the molecule doesn't move entirely out of the probe volume.

The invention may be better understood with the accompanying figures. Similar or identical structure is identified by identical callouts. FIG. 1 shows a schematic representation of a preferred embodiment apparatus of the invention. Apparatus 10 includes laser 12 that emits a laser beam 14 that is reflected off dichroic 16 and enters back portion 18 of objective lens 20. Objective lens 20 focuses light from laser beam 14 into a sample 22. The laser light excites molecule 24 in sample 22 and induces a fluorescent light emission from the excited molecule 24. Fluorescent light emitted by molecule 24 is collected by objective 20, passes through dichroic 16, and then through tube lens 26. Beamsplitter 28 splits the emitted fluorescent light in half after exiting tube lens 26. Tube lens 26 focuses a portion of the fluorescent light onto a first conjugate image plane 30, and focuses another portion of the fluorescent light onto a second conjugate image plane 32. Half of the emitted fluorescent light travels a first distance D1 from beamsplitter 28 to the first image plane 30. The other half of the fluorescent light emitted by molecule 24 travels a second distance D2 from the beamsplitter 28 to the second image plane 32. First distance D1 and second distance D2 are slightly different so that first image plane 30 examines a "z" section of the optical probe volume that is different from the "z" section examined by second image plane 32. Optical fibers are placed at each image plane. First fiber 34 leads to first photon detector 36, second fiber 38 leads to second photon detector 40, third fiber 42 leads to third photon detector 44, and fourth fiber 46 leads to fourth photon detector 48.

The line connecting the centers of first fiber 34 and second fiber 38 is parallel to the x-axis, whereas the line connecting the centers of third fiber 42 and fourth fiber 46 is parallel to the y-axis, as shown in the Cartesian coordinate diagram portion on the right of FIG. 1. Computer system 50 reads the counts on the detectors and also controls the position of the XYZ piezo positioning stage 52. Computer system 50 records every photon detected while molecule 24 is being tracked and bins the photons for tracking and decision-making purposes. The right hand portion of FIG. 1 shows an idealized projection of the optical fibers back into the sample space. First optical fiber 34 and second optical fiber 38 lie along the x-axis, whereas third optical fiber 42 and fourth optical fiber 46 lie along the y-axis. First optical fiber 34 and second optical fiber 38 lie in the same "z" plane, whereas third optical fiber 42 and fourth optical fiber 46 lie in a separate "z" plane.

Computer system 50 uses molecule-tracking logic based upon a tracking algorithm. In a preferred tracking algorithm for tracking molecule 24 with apparatus 10, molecule 24 is in the center of the optical detection volume. The fluorescent light emitted from molecule 24 is split equally amongst first photon detector 36, second photon detector 40, third photon detector 44, and fourth photon detector 48. If the detectors are integrated for an integration period of, for example, 5 milliseconds, the counts might be, for example, 100 photons on each detector. As molecule 24 moves out from the center of the probe volume, the count distribution would no longer be equal amongst the four detectors. It is a non-equal count distribution amongst the detectors that indicates that molecule 24 has moved away from the center of the optical detection volume. After a period of time, the counts on the detectors are measured and the measurements are used to estimate the direction of particle motion. During the next 5 millisecond (ms) integration period, for example, the counts on the detectors might be as follows: first photon detector 36: 90 photons, second photon detector 40: 110 photons, third photon detector 44: 80 photons, and fourth photon detector 48: 90 photons. The counts on first photon detector 36 and second photon detector 40 are compared in order to determine if molecule 24 has taken a step in the x-direction. During the integration period, second photon detector 40 has more counts than first photon detector 36, so it is determined that a step has occurred in the x-direction that moves molecule 24 closer to second photon detector 40 than to first photon detector 36. A similar decision is made for the y-direction because fourth photon detector 48 has recorded more photons than third photon detector 44, so it is determined that molecule 24 has moved closer to the projection of fourth fiber 46 than it is to the projection of third fiber 42. Lastly, for determining movements in the z-direction, the sum of first photon detector 36 and second photon detector 40, which is 200, is compared to the sum of third photon detector 44 and fourth photon detector 48, which is 170. Based on this comparison, it is determined that molecule 24 has moved in the +Z direction (upward toward objective lens 20. Overall, it has been determined that molecule 24 has moved in the +Z direction, in the +X direction, and in the −Y direction. Based on this information, the piezo stage is moved in the opposite direction that molecule 24 has moved in order to compensate for its travel away from the center of the optical probe volume.

It should be noted that the step size and integration period are variables. At present, an integration time is 5 ms and the stage position is updated about 200 times per second because the molecules are moving fast (several microns per second). For slower motion, such as, but not limited to, the diffusion of receptors on cell membranes, longer integration periods may be used.

Figure 2:
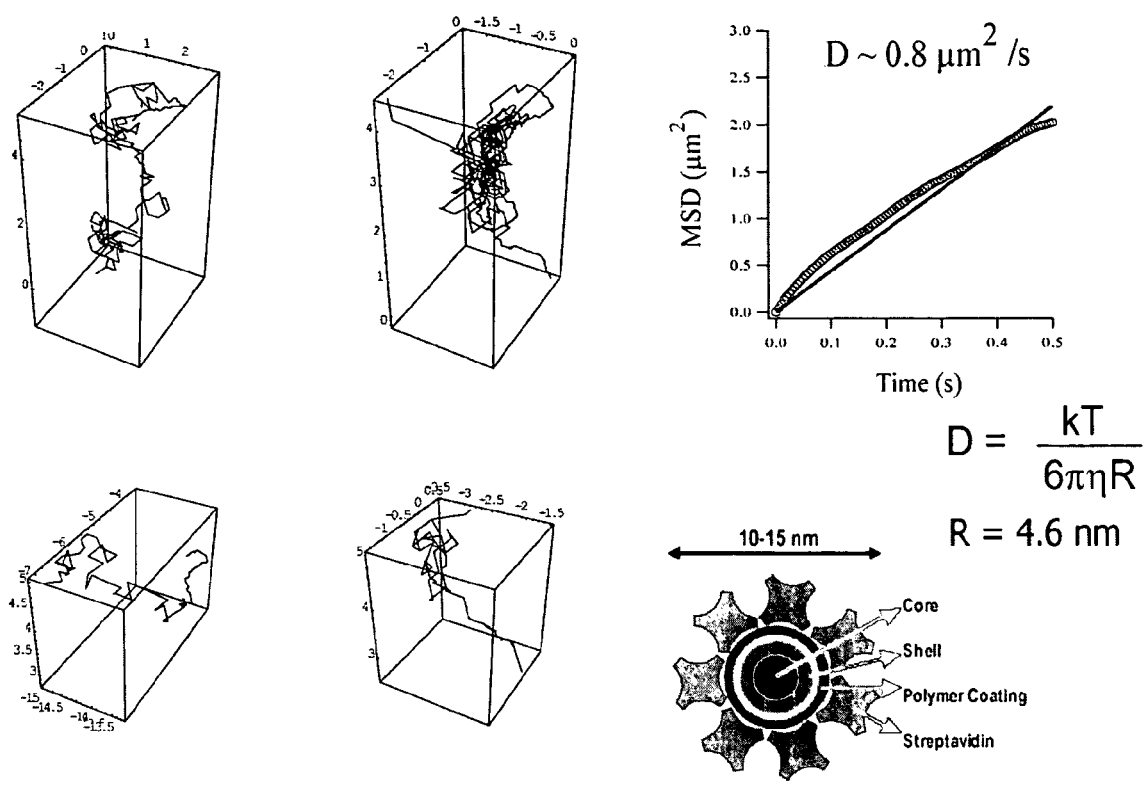
FIG. 2 shows four representative 3-dimensional trajectories that were obtained using an embodiment apparatus of the invention of a fluorescent quantum dot in liquid mixture of 80 percent glycerol and 20 percent water.

The invention has successfully been used to track single quantum dots in a mixture of glycerol and water in three dimensions. The rates for this motion are comparable to the rates expected for, for example, IgE transport through a mast cell. Individual quantum dots having a radius of about 5 nm and a fluorescence emission of about 605 nm were tracked in an 80/20 mixture of glycerol/water. More than 80 trajectories of individual quantum dots were obtained, the trajectories ranging in duration from about 0.2 seconds to over 5 seconds. FIG. 2 shows four representative 3-dimensional trajectories. The units on the axes are in micrometers.

An 80/20 mixture of glycerol/water has a viscosity of about 60 centipoise (cP). From the measured mean squared displacement as a function of time, one can extract an average diffusion coefficient of the particle being tracked. From the measured diffusion coefficient, one can use the Stokes-Einstein relation to calculate a particle radius. This calculation places the radius of the objects that are being tracked at about 5 nm, which in excellent agreement with the size of an individual quantum dot having a radius of about 5-7 nm. It should be noted that the quantum dot in FIG. 2 has a streptavidin protein coat. The radii of the quantum dots used here had a biotin coat and are expected to be somewhat smaller.

The invention may be used to study the spatial and temporal dynamics of, for example, intracellular protein trafficking, receptor mediated endocytosis, or protein-protein association, or be used to examine the conformation of individual protein or RNA molecules without resorting to immobilization. In an EXAMPLE, the apparatus may be used to track the motion of single IgE molecules. The movement of a single IgE molecule labeled with a fluorescent quantum dot [11] could be tracked through a mast cell using an embodiment apparatus of the invention.

Figure 3:
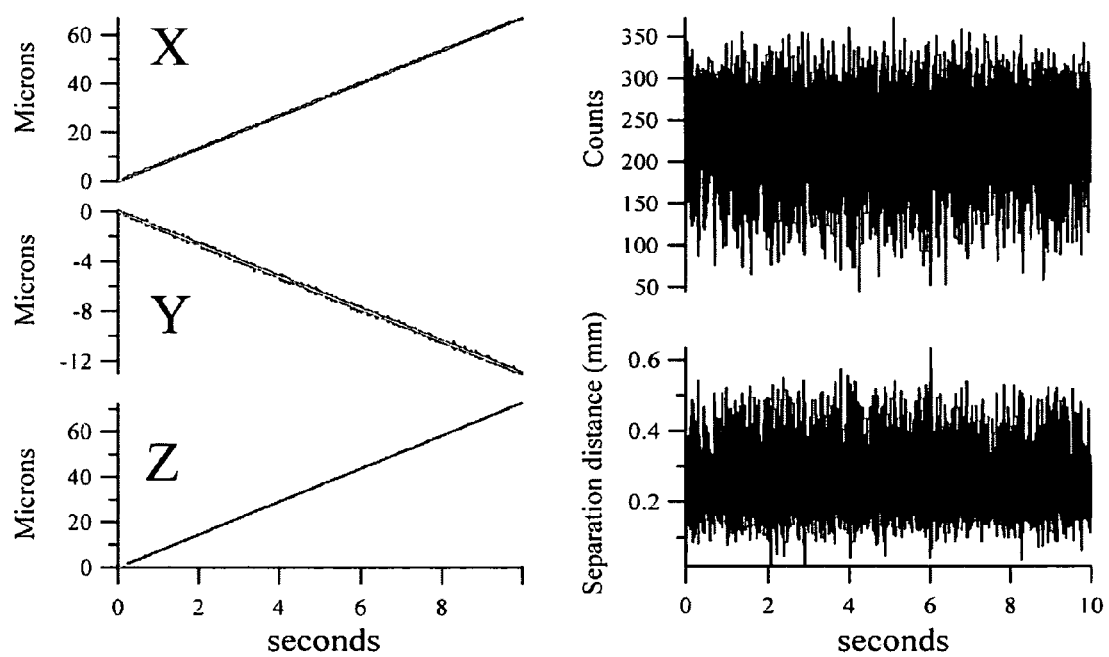
FIG. 3 shows the results of a simulation for tracking a molecule that is moving in a randomly chosen direction at a total velocity of 10 µm/s. The molecular trajectory and the distance separating the molecule from the center of the optical probe volume are shown.

The invention is also concerned with a tracking algorithm that is used for determining how to move the piezo stage. The tracking algorithm is useful for both Brownian motion, and directed movement, of a particle or molecule. FIG. 3 shows the results of a Monte Carlo simulation for tracking a molecule that is moving in a randomly chosen direction at a total velocity of 10 $\mu$m/s. The molecular trajectory, the sum of the counts on all four detectors, and the distance separating the molecule from the center of the optical probe volume are shown. The "hot potato" tracking algorithm seems to be robust in its ability to follow different types of motion such as Brownian motion and/or directed motion.

Quantum dots are preferred fluorophores versus conventional organic fluorophores as fluorescent labels for monitoring individual protein movement in cells because of their increased photostability, among other reasons. Quantum dots, rather than conventional organic fluorophores, have greatly improved the observation time possible for individual labeled molecules from tens of seconds to tens of minutes and this photodegradation time is what limits the temporal duration of our single molecule trajectories. In addition to photobleaching, quantum dots might be "lost" due to blinking. The situation of a quantum dot blinking out is similar to having the molecule escape the probe volume. In both cases (escape or blinking out), the counts fall below a threshold value and the tracking software has the stage raster scan in a "holding pattern" around the last known spatial location of the molecule. The quantum dot may be reacquired almost as soon as luminescence resumes.

Figure 4:
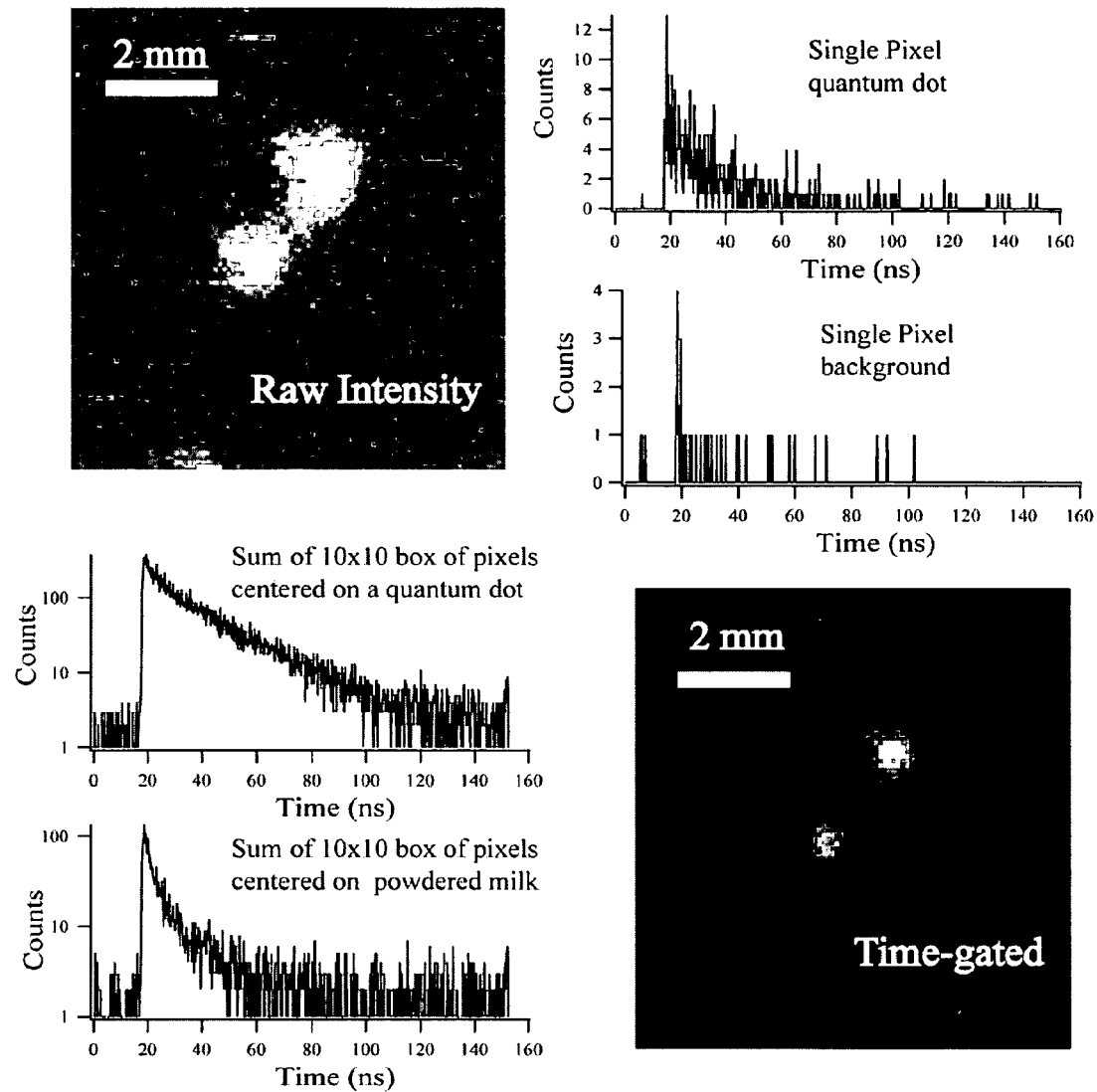
FIG. 4 shows an image of two single immobilized quantum dots (CdSe dots with 585 nm emission) taken with an embodiment apparatus.

In addition to tracking single fluorophores, the instrument can be used as a sensitive confocal microscope, potentially with time-correlated photon counting capabilities. FIG. 4 shows an image of two single immobilized quantum dots (CdSe dots with 585 nm emission) taken with an embodiment apparatus. To simulate backgrounds worse than those anticipated in a cell, a very large dosing of powdered milk of roughly the concentration recommended on the box to make a glass of prepared milk was added to the quantum dots prior to their evaporation on a glass coverslip. FIG. 4 shows histograms of photon arrival times taken while raster scanning over immobilized quantum dots in a background of powdered milk. The experimental conditions were as follows: 437 nm wavelength excitation, 5 microwatts (uW) laser power, 50 picoseconds (ps) pulse width, 1 MHz rep-rate, 10 ms integration time per pixel.

The histogram of photon arrival times for a single pixel of background demonstrates the binary nature of the data that is archived. Fluorescence is recorded in a raw photon counting mode. While photons are counted in discrete time intervals for tracking purposes, the temporal information provided by the tracking apparatus is not limited to this integration period because the tracking apparatus also records the arrival time of individual photons.

Two independent logic processors are used with a preferred embodiment. One of the processors handles tracking, counting photons in discrete time bins, and telling the stage where to go with a fast I/O board. Another processor records every photon detected using a time correlated, single photon-counting (TCSPC) card (for example, an SPC630 TCSPC card obtained from BECKER-HICKL) that records the arrival time of a detected photon with respect to the laser pulse and the arrival of the photon with respect to a 20 MHz macroscopic clock and which detector the photon came from. Storing the data in this raw photon mode enables the use any post-processing or data analysis technique on the same data set, such as fluorescence correlation, time-correlated single photon counting, photon pair correlation (anti-bunching), or photon-by-photon lifetime correlations. Moreover, our time resolution isn't limited to the "frame-rate" of a camera. We will have a window on dynamic processes in a cell that could potentially span 13 orders of magnitude in time (100 picoseconds from lifetime measurements to 1000 seconds, the timescale of the followed trajectory).

The invention may allow the observation of different motions for different modes (diffusive mode or active mode) of transport in a cell. A detailed analysis of a 3-dimensional trajectory could be used to classify different intracellular transportation methods. For example, the apparatus could be used to determine whether a chosen protein is being carried directly to a different site of the cell, or is traveling randomly by Brownian motion.

The invention may also be used for tracking discrete steps of, for example, motor proteins in vivo. Different molecular motors have different transport velocities and step sizes (about 8 nm for kinesin, and about 37 nm for myosin V). Depending upon the absolute tracking accuracy, individual steps of proteins may be observed inside of a cell.

Confocal excitation/detection is important for 3-dimensional tracking because it can spatially filter the excitation volume in three dimensions to about 1 femtoliter in volume (1 fL=1 $\mu$m$^3$). In addition to enabling 3-dimensional sectioning, the use of confocal excitation/detection provides the advantage of a lowered background compared to wide field microscopy. The background in fluorescence microscopy (be it Raman scatter or autofluorescence) scales as the volume of fluid probed. Confocal excitation/detection should have much better signal to noise than single dot tracking that uses wide field imaging confocal excitation/detection also enables the use of two-photon excitation for these tracking studies. Two-photon excitation has the potential for lower backgrounds. Regardless of background considerations, two-photon excitation may be a preferred excitation method for tracking quantum dot-labeled molecules because two-photon excitation reduces photo-damage to the cell. Quantum dots have large two-photon cross sections and are readily detectable at the single molecule level. Thus, either one-photon excitation or two-photon excitation may be used.

The location of a protein in Cartesian coordinate space is very useful when the location can be correlated with an intracellular location. The tracking apparatus of the invention can perform standard raster-scans to build an image but only when the apparatus is not tracking a molecule. However, forming an image after s tracking a molecule is possible.

In an embodiment, a tracking apparatus of the invention may be modified in order to enable simultaneous wide-field imaging with single quantum dot tracking. Wide field images (phase contrast, differential interference contrast, dark field, fluorescence, for example) could be overlaid with the measured trajectory.

Embodiment algorithms used with the invention were designed for following fast Brownian (random) movement in three dimensions. The Monte-Carlo simulations suggest that the same algorithms also work for directed motion. The algorithms can still be refined. Tracking algorithms may be changed "on the fly" based upon the prior history of moves. If the movement of a molecule being tracked appears to be unidirectional along a particular vector (as it would for dyenin or kinesin transport on a microtubule, for example), this knowledge may be used to guess the next spatial location for the molecule. This could be used to follow much faster transport in the cell, as one isn't just relying on the photon counts during the detector integration period, but instead on the entire fluorescence time history.

Once a best estimate of the X,Y,Z position of a molecule as a function of time is obtained, the motion of the molecule may be classified. A preferred method for classifying the motion in single particle tracking is calculating a mean-squared displacement as a function of time from the measured trajectory [1]. Mean squared displacements (MSDs) that grow linearly with time reflect diffusion, whereas a MSD that grows quadratically with time reflects a constant linear velocity. Power-law dependencies of the MSD versus time are also common. There might be distinct switches in the transport modality (diffusion, actin-facilitated recruitment to a clathrin pit, internalization and transport along the microtubule network) that reflect the molecule's current spatial location. Different time slices of the trajectory could be examined and the motion could be determined during each of the time-slices.

In summary, fluorescent quantum dots have been tracked in three dimensions using a confocal microscope that can do much more than standard confocal microscopes of the prior art. Control software for implementing a tracking algorithm has been used for tracking the Brownian motion of individual quantum dots in glycerol/water mixtures. Monte Carlo simulations of the microscope suggest that tracking algorithms used to track particles undergoing Brownian motion in three dimensions may be used to track the directed motion anticipated for single fluorescent or fluorescently labeled biomolecules and thus will be important in answering questions relating to mechanisms of intracellular transport.

The foregoing description of the invention has been presented for purposes of illustration and description and is not intended to be exhaustive or to limit the invention to the precise form disclosed, and obviously many modifications and variations are possible in light of the above teaching. For example, while a preferred embodiment described herein uses two image planes and two spatial filters per image plane, it should be understood that other embodiments of the invention may use more than two image planes and that these would require additional spatial filters and photon detectors (i.e. light detectors, fluorescence detectors). In addition, the approach outlined previously for the 3-dimensional tracking of a molecule or particle involved using small arrays of single photon-counting avalanche photodiodes (SPADs) to sense and measure displacements in a confocal optical detection volume. In a preferred embodiment, four of these photodiodes are used. These four photodiodes are arranged in two separate image planes (each plane has 2 detectors), with these 2 image planes being slightly offset in the "z" direction are used to sense displacements of a molecule or particle from the center of a detection volume. It should be understood that there are other ways of creating two slightly offset image planes that are within the scope of the present invention. One of these is to use a beamsplitter and have different distances from the focusing optic (tube lens) of the microscope system leading to the different image planes. The beamsplitter could split the light equally, into two detection arms, or could split the light based upon the polarization of the fluorescence emission. By resolving the polarization components of the emission, it is possible to measure molecular orientation and Cartesian coordinate position. In another way to create slightly offset image planes, a fiber bundle or spatial detector array used for spatial filtering having elements that are slightly offset from one another along the optical axis is used, where each of the spatial filtering elements images a different "z" section in the optical probe volume. Finally, it should be understood that regardless of the arrangement of the spatial filters or beamsplitter element used, the confocal nature of the optical detection process provides the necessary speed, 3-dimensional sectioning capability, and detection sensitivity for tracking single molecules as they move in three dimensions.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

REFERENCES

The following references are incorporated by reference herein.

1. Saxton et al., "Single-Particle Tracking: Applications to Membrane Dynamics," in Annual Review of Biophysics and Biomolecular Structure, (1997), vol. 26, pp. 373-399.
2. Kao et al., "Tracking of Single Fluorescent Particles in 3 Dimensions: Use of Cylindrical Optics to Encode Particle Position," Biophysical Journal, (1994), vol. 67, no. 3, pp. 1291-1300.
3. Dickson et al., "Three-Dimensional Imaging of Single Molecules Solvated in Pores of Poly(acrylamide) Gels," Science, (1996) vol. 274 (5289), pp. 966-969.
4. Braun et al., "Fluorescence Interference-Contrast Microscopy of Cell Adhesion on Oxidized Silicon," Applied Physics A (Materials Science Processing), (1997), vol. 65(4/5), pp. 341-348.
5. Ajo-Franklin et al., "Variable Incidence Angle Fluorescence Interference Contrast Microscopy for Z-Imaging Single Objects," Biophysical Journal, (2005), vol. 89, no. 4, pp. 2759-2769.
6. Prabhat et al., "Simultaneous Imaging of Different Focal Planes in Fluorescence Microscopy for the Study of Cellular Dynamics in Three Dimensions," IEEE Transactions on Nanobioscience, (2004), vol. 4, no. 4, pp. 237-242.
7. Enderlein, "Tracking of Fluorescent Molecules Diffusing Within Membranes," Applied Physics B-Lasers and Optics, (2000), vol. 71, no. 5, pp. 773-777.
8. Enderlein, "Positional and Temporal Accuracy of Single Molecule Tracking," Single Molecules, (2000), vol. 1, no. 3, pp. 225-230.
9. Levi et al., "3-d Particle Tracking in a Two-Photon Microscope: Application to the Study of Molecular Dynamics in Cells," Biophysical Journal, (2005), vol. 88, no. 4, pp. 2919-2928.
10. Visscher et al., "Versatile Optical Traps With Feedback Control, Methods in Enzymology; Molecular Motors and the Cytoskeleton, part b, (1998), vol. 298, pp. 460-489, R. Vallee, Editor, 1998, 14 Belgrave Square, 24-28 Oval Road, London NW1 7OX, England, UK: Academic Press Ltd.
11. Michalet et al., "Quantum Dots for Live Cells, In Vivo Imaging, and Diagnostics," Science, (2005), vol. 307(5709), pp. 538-544.

What is claimed is:

1. An apparatus for tracking the position of a molecule or particle in a sample, comprising:
    a stage for supporting the sample,
    a light source for emitting a light beam capable of inducing a measurable light-based response from a chosen molecule or particle in the sample,
    an objective lens for focusing the light beam on the sample to create an excitation volume, said objective lens projecting at least a portion of the light based response from the excitation volume to at least one image plane,
    a dichroic element for directing the light beam from the light source to the objective lens,
    at least one spatial filter at the at least one image plane for selecting a portion of the light based response and defining an optical probe volume for that portion of the light based response,
    means for introducing a controlled relative motion between the optical probe volume and the molecule or particle, and
    means for monitoring the light based response from the chosen molecule or particle, wherein said means for monitoring the light based response uses the light based response to control an overlap between the optical probe volume with the particle or molecule being tracked.

2. The apparatus of claim 1, wherein said means for monitoring the light based response comprises a plurality of photon detectors that detect light the light based response from the molecule or particle in combination with a computer system that uses the detected light based response from the photodetectors to determine how said apparatus should be adjusted to maintain the molecule or particle being tracked in the optical probe volume.

3. An apparatus for tracking the position of a molecule or particle in a sample, comprising:
    a stage for supporting the sample,
    a light source for emitting a light beam capable of inducing a light based response from a chosen molecule or particle in a sample,
    an objective lens for focusing the light beam on the chosen molecule or particle in the sample,
    means for introducing a controlled lateral displacement between said light source and said stage,
    a dichroic element for directing the light beam from said light source to said objective lens,
    means for creating at least a first image plane and a second image plane, the first image plane including spatial information from a first portion of the sample, the second image plane including spatial information from a second portion of the sample, the first portion and second portion defining an optical probe volume,
    a first optical spatial filter that sends light from the first image plane to a first photon detector and a second optical spatial filter that sends light from the second image plane to a second photon detector,
    a first photon detector for receiving light from the first image plane and a second photon detector for receiving light from the second image plane, and
    means for analyzing light from said first photon detector and said second photon detector, wherein said means for analyzing light uses an analysis of light from said first photon detector and said second photon detector to control an overlap between the optical probe volume and the particle or molecule being tracked.

4. The apparatus of claim 3, wherein at least one of said first spatial optical filter and said second spatial optical filter is moveable.

5. The apparatus of claim 3, wherein said means for creating at least a first image plane and a second image plane comprises a beamsplitter or a dichroic filter.

6. The apparatus of claim 3, wherein said means for analyzing light from said first photon detector and said second photon detector comprises a computer system that reads the photon counts from said first photon detector and said second photon detector and uses the photon counts to control the overlap between the optical probe volume and the molecule or particle being tracked, and that uses the detected light based response from the photodetectors to determine how said apparatus should be adjusted to maintain the molecule or particle being tracked in the optical probe volume.

7. The apparatus of claim 3, further comprising a tube lens for focusing a portion of the light emission onto the first image plane, and for focusing another portion of the light emission onto the second image plane.

8. An apparatus for tracking the position of a molecule or particle in a sample, comprising:
    a light source for emitting a light beam capable of inducing fluorescence from a chosen molecule or particle in a sample,
    an objective lens for focusing the light beam on the chosen molecule or particle in the sample,
    a stage for supporting the sample,
    a dichroic element for directing the light beam from the light source to the objective lens,
    means for creating a first image plane and a second image plane, the first image plane including spatial information from a first portion of the sample, the second image plane being nearly conjugate with the first image plane and including spatial information from a second portion of the sample, the first portion and second portion defining an optical probe volume,
    a first optical fiber that sends light from the first image plane to a first photon detector, the first optical fiber having a cross-section with a center,
    a second optical fiber that sends light from the first image plane to a second photon detector, the second optical fiber having a cross-section with a center, wherein a line connecting the center of the first optical fiber and the center of the second optical fiber is parallel to the x-axis,
    a third optical fiber that sends light from the second image plane to a third detector, the third optical fiber having a cross-section with a center, a fourth optical fiber that sends light from the second image plane to a fourth detector, the fourth optical fiber having a cross-section with a center, wherein a line connecting the center of third optical fiber and the center of the fourth optical fiber is parallel to the y axis, and means for reading photon counts from fluorescence detected by said first detector and said second detector and said third detector and said fourth detector, wherein said means for reading photon counts uses the photon counts to control the overlap between the optical probe volume and the particle or molecule being tracked.

9. The apparatus of claim 8, wherein at least one of said first optical fiber, said second optical fiber, said third optical fiber, and said fourth optical fiber comprises a circular optical fiber.

10. The apparatus of claim 8, wherein said stage is moveable in order to adjust of the position of the particle or molecule being tracked.

11. The apparatus of claim 8, wherein at least one of said first optical fiber, said second optical fiber, said third optical fiber, and said fourth optical fiber is movable.

12. The apparatus of claim 8, wherein said means for creating the first image plane and the second image plane comprises an intensity beamsplitter that splits the fluorescent light emitted from the chosen molecule or particle.

13. The apparatus of claim 8, wherein said means for creating the first image plane and the second image plane comprises a polarization beamsplitter or a dichroic filter.

14. The apparatus of claim 8, wherein said means for reading photon counts from fluorescence detected by said first detector and said second detector and said third detector and said fourth detector and using the photon counts to control the overlap between the optical probe volume and the particle or molecule being tracked comprises a computer system, said computer system comprising computer readable software, wherein said computer system uses the photon counts to control the position of said stage so that the chosen particle or molecule remains substantially in the center of an optical volume.

15. The apparatus of claim 8, wherein said means for reading photon counts from fluorescence detected by said first detector and said second detector and said third detector and said fourth detector comprises a field programmable gate array (FPGA).

16. The apparatus of claim 8, further comprising a tube lens for focusing light collected from the objective lens alternately onto the first image plane and onto the second image plane.

17. A method for tracking the position of a particle or molecule in a sample, comprising:

exposing a sample to light to induce fluorescence from a chosen particle or molecule in the sample, the sample comprising a plurality of z-slices that define an optical probe volume;

analyzing the fluorescence with a first image plane that includes spatial information from a first z-slice from the plurality of z-slices, and with a second image plane that is nearly conjugate with the first image plane; the second image plane including spatial information from a second z-slice from the plurality of z-slices; and using the spatial information from the first image plane and the second image plane to control the overlap of the optical probe volume and the chosen particle or molecule being tracked.

18. A method for tracking the position of a particle or molecule in a sample, comprising:

exposing a sample to light for a chosen period of time to induce light emission from a chosen particle or molecule in the sample;

detecting the light emission using a plurality of detectors; and using the intensity of the light emission to evaluate the distance between the center of an optical probe volume and the chosen molecule or particle being tracked.

19. The method of claim 18, further comprising using the intensity of the light emission to control an overlap of the optical probe volume with the particle or molecule being tracked.

20. A method for tracking a molecule in three dimensions, comprising:

exposing a sample to light for a chosen period of time to induce light emission from a chosen particle or molecule in the sample, detecting the light emission using a plurality of detectors, each of said plurality recording the light emission at a different location near the sample, determining which of the plurality of detectors detected the highest light emission during the chosen period of time, adjusting the position of the sample away from the detector that detected the highest light emission and toward the other detectors of the plurality of detectors.

* * * * *